United States Patent [19]

Kamochi et al.

[11] Patent Number: 5,561,945
[45] Date of Patent: *Oct. 8, 1996

[54] METHOD OF KILLING NOXIOUS INSECTS BY APPLICATION OF INSECTICIDE WITH PLIERS

[75] Inventors: Atsumi Kamochi; Nobuhiro Yamashita; Ikuya Saito, all of Kochi, Japan

[73] Assignee: Nihon Bayer Agrochem K.K., Tokyo, Japan

[ * ] Notice: The term of this patent shall not extend beyond the expiration date of Pat. No. 5,079,334.

[21] Appl. No.: 252,128

[22] Filed: Jun. 1, 1994

[30] Foreign Application Priority Data

Jun. 8, 1993 [JP] Japan ................... 5-163336

[51] Int. Cl.$^6$ .................. A01B 79/00
[52] U.S. Cl. .................. 47/58; 47/1.01; 47/1.5
[58] Field of Search ................ 47/1.5; 424/409

[56] References Cited

U.S. PATENT DOCUMENTS

| 789,659 | 5/1905 | Kantorwicz | 47/15 |
|---|---|---|---|
| 3,891,423 | 6/1975 | Stanley et al. | 71/79 |
| 4,678,795 | 7/1987 | Shiokawa et al. | 514/341 |
| 4,742,060 | 5/1988 | Shiokawa et al. | 514/252 |
| 4,882,874 | 11/1989 | Paulson et al. | 47/1.5 |
| 4,965,960 | 10/1990 | Moore | 47/1.5 |
| 5,032,589 | 7/1991 | Shiokawa et al. | 514/245 |
| 5,051,434 | 9/1991 | Kozo et al. | 514/357 |
| 5,097,560 | 3/1992 | Lawrence | 47/1.5 |

FOREIGN PATENT DOCUMENTS

| 0254196 | 7/1987 | European Pat. Off. . | |
|---|---|---|---|
| 0564945 | 3/1993 | European Pat. Off. . | |
| 176837 | 7/1935 | Switzerland | 47/15 |
| 9104965 | 4/1991 | WIPO . | |

OTHER PUBLICATIONS

Chemical Abstracts, vol. 114, No. 23, 10, Jun. 1991, Abstract No. 22340h.
Abstract of Japanese Patent Application 49–55837.
Abstract of Japanese Patent Application 60–224601.

*Primary Examiner*—Peter F. Kulkosky
*Attorney, Agent, or Firm*—Sprung Horn Kramer & Woods

[57] ABSTRACT

A method of killing noxious insects with the use of either a shaped article having a projection previously coated with a particular active compound or a shaped article having a projection and provided with a spout for discharging said active compound. Pressure is applied from outside onto and around the stalks and/or stems of fruits, vegetables, flowers and ornamental plants, thereby forcibly making the surfaces of said stalks and/or stems absorb the active compound.

5 Claims, No Drawings

METHOD OF KILLING NOXIOUS INSECTS BY APPLICATION OF INSECTICIDE WITH PLIERS

The present invention relates to a method of controlling insects, more particularly, to a method of controlling pests infesting fruits, vegetables, flowers and ornamental plants.

The nitroimino compounds disclosed in Japanese Patent Application Disclosure No. Sho 61-106854 are compounds exhibiting insecticidal activity at extremely low dosages as compared with the known organic phosphorus- and carbamate-series insecticides.

A method is already known in the art wherein unnecessary trees are killed with the use of chemical-immersed carriers or needle-like shaped materials inserted into their trunks (Japanese Patent Application Disclosure Nos. Sho 49-55837 and Sho 60-224601).

Pesticides are used in various kinds of formulations, most of which are applied in the forms of emulsions, wettable powders, dust formulations and granules.

The conventional spraying and dusting applications pose a number of problems, such as soil residues and crop residues of varying contents of pesticides, hazardous chemical exposure and severe working conditions for the farmers during the application, proliferation of chemicals in the environment, excessive application for retaining chemical effectiveness, working efficiency in application, etc.

The present invention provides a novel method capable of effectively and assuredly controlling insects addressing the aforementioned problems.

Specifically, a method is provided for controlling insects infesting fruits, vegetables, flowers and ornamental plants, which comprises applying pressure from outside onto and around their stalks and/or stems by a shaped article having a projection which has been previously coated with an active compound, or with a shaped article having a projection and provided with a spout for discharging said active compound therethrough, so as to make the surfaces of said stalks and/or stems absorb said active compound, wherein said active compound is represented by the following general formula (I)

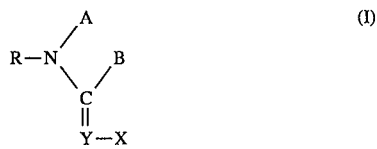

wherein
R represents hydrogen, acyl, alkyl or optionally substituted heteroarylalkyl,
A represents hydrogen, alkyl or a divalent group connected to B,
B represents alkyl,

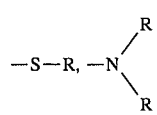

or a divalent group or atom connected to A,
Y represents

or =C—, wherein $T^1$ represents hydrogen or optionally substituted alkyl, and
X represents an electron attracting group.

The compounds represented by the general formula (I) according to the method of killing noxious insects of the present invention are already known in the art, e.g. Japanese Patent Application Disclosure Nos. Sho 60-218386, Sho 61-178981, Sho 61- 267575, Sho 62-81382, Hei 2-288859, Hei 2-288860, and Hei 2- 235881 as well as WO 91/04965.

The method according to the present invention has surprisingly been found to be excellent in that effective dosages of the active compounds can be greatly reduced, nonetheless with ensured pest control for a long period of time. With regard to environmental pollution, the active compounds can be applied onto the plant bodies without affecting other plant bodies, without fear of leaving soil residue of the active compounds yet with ready dosage control.

In preferred compounds of the general formula (I),
R represents hydrogen, formyl, $C_{1-4}$ alkylcarbonyl, benzoyl, $C_{1-4}$ alkylsulfonyl, $C_{1-6}$ alkyl, or optionally substituted heteroarylmethyl wherein the hetero has up to six ring atoms of which at least one is a nitrogen atom,
A represents hydrogen, $C_{1-6}$ alkyl or ethylene, trimethylene, or

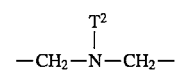

connected to B, wherein $T^2$ represents hydrogen, $C_{1-4}$ alkyl or $C_{1-4}$ alkylcarbonyl,
B represents $C_{1-6}$ alkyl, —S—R,

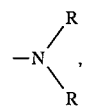

—S—, or methylene or

connected to A, wherein R and $T^2$ have the same meanings as defined above,
Y represents =N— or =CH— and
X represents nitro or cyano.

In more preferred compounds,
R represents hydrogen, formyl, acetyl, $C_{1-4}$ alkyl, 2-chloro-5-pyridylmethyl or 2-chloro-5-thiazolyl,
A represents hydrogen, $C_{1-4}$ alkyl, or ethylene, trimethylene, or

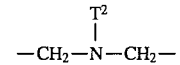

connected to B, wherein $T^2$ represents methyl or ethyl,
B represents $C_{1-4}$ alkyl, —S—R,

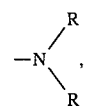

or —S—, methylene or

connected to A, wherein R and $T^2$ have the same meanings as defined above,

Y represents =N—, or =CH—, and
X represents nitro or cyano.

In particularly preferred compounds,
R represents 2-chloro-5-pyridylmethyl or 2-chloro-5-thiazolylmethyl,
A represents hydrogen, $C_{1-4}$ alkyl or ethylene, trimethylene, or

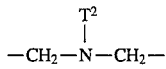

connected to B, wherein $T^2$ represents methyl or ethyl,
B represents $C_{1-4}$ alkyl —S—R,

or —S—, methylene, or

connected to A, wherein R and $T^2$ have the same meanings as defined above,
Y represents =N— or =CH—, and
X represents nitro or cyano.

As concrete examples of compounds of the general formula (I) to be employed according to the present method of killing noxious insects, the following compounds may be mentioned:

1-(6-chloro-3-pyridylmethyl)-N-nitro-imidazolidine-2-ylideneamine,
N-cyano-N-(2-chloro-5-pyridylmethyl)-N'-methylacetoamidine,
1-[N-(6-chloro-3-pyridylmethyl)-N-ethylamino]-1-methylamino- 2-nitroethylene,
1-(2-chloro-5-pyridylmethyl)-5-methyl-2-nitroiminohexahydro- 1,3,5-triazine,
1-(2-chloro-5-thiazolylmethyl)-3,5-dimethyl-2-nitroiminohexahydro- 1,3,5-triazine,
1-(2-chloro-5-pytidylmethyl)-3,5-dimethyl-2-nitroiminohexahydro- 1,3,5-triazine,
1-(2-chloro-5-pyridylmethyl)-2-nitromethylene-imidazolidine,
1-[N-(2-chloro-5-thiazolylmethyl)-N-ethylamino]-1-methylamino-2-nitroethyleno,
3-(2-chloro-5-pyridylmethyl)-2-nitromethylene-thiazolidine,
1-(2-chloro-5-pyridylmethyl)-2-(1-nitro-2-allylthioethylidene)imidazolidine,
1-(2-chloro-5-pyridylmethyl)-2-(1-nitro-2-ethylthioethylidene)imidazolidine,
1-(2-chloro-5-pyridylmethyl)-2-(1-nitro-2-β-methylallylthioethylidene)imidazolidine,
methyl-[[3-(2-chloro-5-pyridylmethyl)-1-methyl-2-nitro]-guanidinoformate,
1-(2-chloro-5-pyridylmethylamino)-1-methylthio-2-nitroethylene,
1-(2-chloro-5-pyridylmethylamino)-1-methylamino-2-nitroethylene,
1-(2-chloro-5-pyridylmethyl)-3-nitro-2-methylisothiourea,
3-(2-chloro-5-pyridylmethyl)-1-methyl-2-nitroguanidine,
1-(2-chloro-5-pyridylmethylamino)-1-dimethylamino-2-nitroethylene,
1-[N-(2-chloro-5-pyridylmethyl)-N-methylamino]-1-methylamino-2-nitroethylene,
1-[N-(2-chloro-5-pyridylmethyl)-N-methylamino]-1-dimethylamino- 2-nitroethyleno,
3-(2-chloro-5-pyridylmethyl)-1,1-dimethyl-2-nitroguanidine,
1-(2-chloro-5-pyridylmethylamino)-1-ethylamino-2-nitroethylene,
1-amino-1-[N-(2-chloro-5-pyridylmethyl)-N-methylamino]-2-nitroethylene,
3-(2-chloro-5-pyridylmethyl)-1,3-dimethyl-2-nitroguanidine,
3-(2-chloro-5-pyridylmethyl)-1,1,3-trimethyl-2-nitroguanidine,
1-amino-1-[N-(2-chloro-5-pyridylmethyl)-N-ethylamino]-2-nitroethylene,
1-[N-(2-chloro-5-pyridylmethyl)-N-ethylamino]-1-methylamino- 2-nitroethylene,
1-[N-(2-chloro-5-pyridylmethyl)-N-n-propylamino]-1-methylamino-2-nitroethylene,
1-[N-(chloro-5-pyridylmethyl)-N-ethylamino]-1-ethylamino-2-nitroethylene, and
3-(2-chloro-5-pyridylmethyl)-3-ethyl-1-methyl-2-nitroguanidine,
and so on.

The above named compounds are only representative examples of compounds represented of the general formula (I), which, therefore, should not be taken as limiting the method of killing noxious insects according to the present invention.

As concrete examples of fruits, vegetables, flowers and ornamental plants to be treated according to the present invention may be mentioned fruits and vegetables such as eggplant, cucumber, tomato, melon, watermelon, green pepper, hop, and the like, and flowers and ornamental plants such as chrysanthemum, rose, and the like.

As concrete examples of noxious insects effectively and assuredly to be controlled according to the method of the present invention there may be mentioned Homoptera such as aphids, e.g. cotton aphid (*Aphis gossypii*), Green peach aphid (*Myzus persicae*), etc., and Thysanoptera represented by Minamikiiro Azamiuma (*Thrips palmi* Karny).

However, the method of killing noxious insects according to the present invention is not limited only to the application to the above-mentioned noxious insects but can widely be applied for the control of pests damaging vegetables and horticultural crops of flowers and ornamental plants in general.

The effective dosage of the active component according to the method of the present invention is in the range of from about 2.0 mg to about 7.0 mg, preferably from about 3.0 mg to about 6.0 mg, per plant body but it may be suitably varied depending on the growth conditions of the plants under cultivation and degree of insect infestation.

In applying the method according to the present invention to the plants to be treated, with the use of either a shaped article having a projection and previously coated with the active compound represented by the general formula (I) or a shaped article having a projection and provided with a spout for discharging said active compound pressure is applied outside onto and around the stalks and/or stems of fruits, vegetables, flowers and ornamental plants, thereby forcibly making the surfaces of said stalks and/or stems absorb the active compound.

In this connection, the meaning of "forcibly absorb" includes a case where onto the surfaces of stalks of a plant body such pressure is applied by an article including a projection such as a needle or nail, or surface pressure is caused by an uneven surface of a driven article.

Preferred examples of such a shaped article having a projection as employed according to the present invention include "Kenzan" (a hedgehog-like frog to be used in flower arrangements as a flower stem holder), a kenzan-like article, concave pinching surfaces of a plier head and all like tools capable of achieving the same function. Further, in preferred examples of a shaped article having a spout there may be mentioned articles having a projected forward end having a very small opening, from which a very small capillary extends to a storage chamber provided in the article body for storing active component.

However, the shaped articles to be employed according to the method of the present invention are not limited only to those mentioned above and include whatever can achieve the effect called for in the present invention.

The materials form which the shaped articles of the present invention are made include iron, aluminum, plastics, hard rubber, and like materials so far as they can achieve the method of the present invention.

As formulations of the active compounds represented by the general formula (I) according to the present method there may be mentioned solutions, emulsions, suspensions, liquid and micro-capsules, and the like.

These formulations may be produced in known manner, for example, by mixing the active compounds with liquid diluents or surface active agents. In the case of using water, organic solvents can, for example, also be used as auxiliary solvents.

As liquid diluents there may be mentioned, in general, aromatic hydrocarbons, such as xylene, toluene and alkyl naphthalenes, chlorinated aromatic or chlorinated aliphatic hydrocarbons, such as chlorobenzenes, chloroethylenes and methylene chloride, aliphatic or alicyclic hydrocarbons, such as cyclohexane or paraffins, for example, mineral oil fractions, alcohols, such as butanol or glycol as well as their ethers and esters, ketones, such as acetone, methyl ethyl ketone, methyl isobutyl ketone or cyclohexanone, etc., or strongly polar solvents, such as dimethylformamide and dimethylsulfoxide, as well as water.

As surface active agents there may be mentioned nonionic and anionic surface active agents, such as polyoxyethylene-fatty acid esters, polyoxyethylene-fatty alcohol ethers, for example, alkylaryl polyglycol ethers, alkylsulfonates, alkylsulfates, arylsulfonates as well as albumin hydrolysis products.

It is possible to include colorants such as inorganic pigments, for example, iron oxide, titanium oxide and Prussian Blue, and organic dyestuffs, such as alizarin dyestuffs, azo dyestuffs or metal phthalocyanine dyestuffs, and trace elements, such as salts of iron, manganese, boron, copper, cobalt, molybdenum and zinc.

The formulations, for example, contain from 0.1 to 95 percent by weight of active compound, preferably from 0.5 to 90 percent by weight.

The shaped articles to be employed in the method of the invention may comprise, in addition to the active compounds represented by the general formula (I), other active compounds such as insecticides, fungicides, acaricides, plant growth regulators, etc., if desired. Those active compounds are suitable which exhibit systemic action in plant bodies and, as examples, there may be mentioned the following representative chemicals:

triazimefon, bitertanol, fenarimol, tebuconazole, prochloraz, triflumizole, pyrifenox, triforine, pefurazoate, hexaconazole, myclobutanil, propiconazole, diniconazole, fenpropimorph, bromuconazole, and the like.

Next, the present invention will be illustrated in the following examples but it should be noted that the scope of the present invention is not limited only to that which is described in the examples.

EXAMPLE

Compound under test

No. 1:
1-(6-chloro-3-pyridylmethyl)-N-nitro-imidazolidine-2-ylideneamine

Text:

Control of Cotton Aphid (*Aphis gosyppi*)

Test Method:

Eggplants (Ryoma species) each grown to a height of about 50 cm were allowed to be naturally infested with cotton aphids having resistances to organic phosphorus compositions and carbamate compositions.

Under such conditions that the adult insects infested each of the test plants at a rate of around 110 pieces per plant, a flowable agent containing 20% of the above-mentioned active compound No. 1 was coated onto the forward end of a pliers at a predetermined dosage, followed by press treatment therewith on the stalk portion of the plant at a height of about 7 cm above the soil surface. The test plants were allowed to stand at 20° C. (±2° C.) in a hothouse, and then the number of surviving insects was determined three, eight, fourteen, twenty-one, twenty-eight and thirty-five days, respectively, after the treatment, then calculating the control effect in % according to the following equation: The results of the test is shown in Table 1.

As in the foregoing test example, a test was carried out on eggplants each having a height of about 1 m, the thus obtained results being shown in Table 2.

$$\text{Control effect (\%)} = 1 - \frac{\text{the number of surviving insects in a test section after treatment} \times \text{the initial number of live insects in an untreated section}}{\text{the number of live insects in the test section before treatment} \times \text{the number of live insects in the untreated section at the time of counting in the treated test section}} \times 100$$

TABLE 1

| Concentration of the active component | Control Effect (%) Days after treatment | | | | | | |
|---|---|---|---|---|---|---|---|
| mg/plant body | 0 | 3 | 8 | 14 | 21 | 28 | 35 |
| 3 | — | 97.5 | 100 | 98.5 | 98 | 89 | 68.5 |
| 6 | — | 98.5 | 100 | 98 | 98 | 87.5 | 78.5 |
| Comparison Spray treatment | — | 99.5 | 100 | 95.5 | 82.5 | 0 | 0 |
| | | | Number of insects | | | | |
| Untreated | 110 | 307 | 904 | 1697 | 1459 | 652 | 303 |

Remark: In "Spray treatment", the same active compound was used in a concentration of 50 ppm.

TABLE 2

| Concentration of the active component | Control Effect (%) Days after treatment | | | | |
|---|---|---|---|---|---|
| mg/plant body | 0 | 3 | 7 | 14 | 21 | 28 |
| 3 | — | 51.5 | 98.5 | 98.5 | 95 | 88 |
| 6 | — | 56.5 | 97.5 | 97.5 | 95 | 91.5 |
| Comparison Spray treatment | — | 98.5 | 99.5 | 97.5 | 89 | 64 |
| | Number of insects (per thirty leaves) | | | | |
| Untreated | 561 | 1546 | 3431 | 10936 | 21018 | 17867 |

The method according to the present invention is a major advance in controlling pests infesting fruits, vegetables, flowers and ornament plants and, by employing the present method, various pests can be assuredly controlled, with high efficiency and favorable environmental conditions.

It is understood that the specification and examples are illustrative but not limitative of the present invention and that other embodiments within the spirit and scope of the invention will suggest themselves to those skilled in the art.

We claim:

1. A method of controlling pests infesting fruits, vegetables, flowers and ornamental plants, which comprises applying pressure from outside and onto and around at least one of their stalks and stems with a pliers coated with a composition containing an active compound in a concentration of about 0.1 to 95%, whereby the surfaces of said stalks and stems absorb said active compound in about 2–7 mg per plant, said active compound having the formula

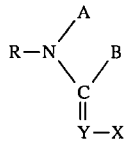
(I)

wherein

R represents hydrogen, acyl, alkyl or optionally substituted heteroarylalkyl,

A represents hydrogen, alkyl or a divalent group connected to B,

B represents alkyl, —S—R,

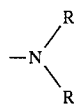

or a divalent group or atom connected to A,

Y represents =N— or

wherein $T^1$ represents hydrogen or optionally substituted alkyl, and

X represents an electron attracting group, wherein improved effectiveness is achieved in toxicity against noxious insects as compared to treatment with the same composition by spray of other surface application methods.

2. The method according to claim 1, wherein

R represents hydrogen, formyl, $C_{1-4}$ alkylcarbonyl, benzoyl, $C_{1-4}$ alkylsulfonyl, $C_{1-6}$ alkyl, or optionally substituted heteroarylmethyl wherein the hetero has up to six ring atoms of which at least one is a nitrogen atom, A represents hydrogen, $C_{1-6}$ alkyl or ethylene, trimethylene, or

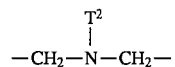

connected to B, wherein $T^2$ represents hydrogen, $C_{1-4}$ alkyl or $C_{1-4}$ alkylcarbonyl, B represents $C_{1-6}$ alkyl, —S—R,

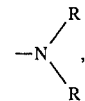

or —S—, methylene or

connected to A,

Y represents =N— or =CH— and

X represents nitro or cyano.

3. The method according to claim 2, wherein

R represents hydrogen, formyl, acetyl, $C_{1-4}$ alkyl, 2-chloro-5-pyridylmethyl or 2-chloro-5-thiazolyl, A represents hydrogen, $C_{1-4}$ alkyl, or ethylene, trimethylene, or

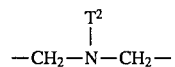

connected to B, wherein $T^2$ represents methyl or ethyl, and

B represents $C_{1-4}$ alkyl, —S—R,

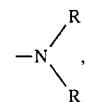

or —S—, methylene or

connected to A.

4. The method according to claim 3, wherein

R represents 2-chloro-5-pyridylmethyl or 2-chloro-5-thiazolylmethyl,

A represents hydrogen, $C_{1-4}$ alkyl or ethylene, trimethylene, or
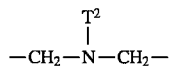
connected to B, wherein $T^2$ represents methyl or ethyl, and
B represents $C_{1-4}$ alkyl, —S—R,
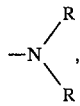
—S—, or methylene or
connected to A.
5. The method according to claim 1, wherein the active compound is 1-(6-chloro-3-pyridylmethyl)-N-nitroimidazolidine-2-ylideneamine.
* * * * *

UNITED STATES PATENT AND TRADEMARK OFFICE
CERTIFICATE OF CORRECTION

PATENT NO. : 5,561,945
DATED : October 8, 1996
INVENTOR(S) : Kamochi, et al.

It is certified that error appears in the above-indentified patent and that said Letters Patent is hereby corrected as shown below:

Title Page   After " [45] Date of Patent:   delete " * "

Title Page   Delete " [*] Notice:  The term of this patent shall not extend beyond the expiration date of Pat. No. 5,079,334. "

Signed and Sealed this

Thirteenth Day of May, 1997

Attest:

BRUCE LEHMAN

Attesting Officer             Commissioner of Patents and Trademarks